United States Patent [19]

Ediger et al.

[11] Patent Number: 5,582,185
[45] Date of Patent: Dec. 10, 1996

[54] DEVICE FOR EVALUATING OPTICAL ELEMENTS BY REFLECTED IMAGES

[75] Inventors: Marwood N. Ediger, Vienna, Va.; Laurence Grossman, Olney, Md.

[73] Assignee: The United States of America as represented by the Department of Health and Human Services, Washington, D.C.

[21] Appl. No.: 685,399

[22] Filed: Apr. 16, 1991

[51] Int. Cl.$^6$ .................................................. A61B 3/103
[52] U.S. Cl. ........................ 128/774; 606/10; 356/124.5; 356/125
[58] Field of Search ......................... 606/2, 10; 128/395, 128/774; 356/124, 24.5, 125, 127

[56] References Cited

U.S. PATENT DOCUMENTS

| | | |
|---|---|---|
| 2,385,503 | 9/1945 | Glasser . |
| 3,572,939 | 3/1971 | Burdick .................................. 356/124 |
| 4,149,801 | 1/1979 | Volk ........................................ 356/124 |
| 4,293,198 | 10/1981 | Kohayakawa et al. .................. 351/13 |
| 4,533,222 | 8/1985 | Ishikawa ................................. 351/206 |
| 4,660,946 | 4/1987 | Nakamura et al. ..................... 351/212 |
| 4,666,269 | 5/1987 | Nakamura et al. ..................... 351/212 |
| 4,679,917 | 7/1987 | Genco et al. .......................... 351/211 |
| 4,710,003 | 12/1987 | Masuda et al. ........................ 351/211 |
| 4,938,584 | 7/1990 | Suematsu et al. ..................... 351/211 |

FOREIGN PATENT DOCUMENTS 467459  1/1992  European Pat. Off. ................... 606/7

OTHER PUBLICATIONS

Webster's dictionary pp. 1429 and 2640.

Primary Examiner—David M. Shay
Attorney, Agent, or Firm—Lowe, Price, LeBlanc & Becker

[57] ABSTRACT

A method and apparatus for evaluating optical elements which utilizes reflected images. The method allows determination of the optical effects contributed by individual surfaces of a single optical alone or in a multiple element optical system. The method is particularly useful for evaluating corneas after transplant, grafting and reshaping procedures.

7 Claims, 2 Drawing Sheets

N=123  MEAN=149.03  WIDTH=202

DEVICE FOR EVALUATING OPTICAL ELEMENTS BY REFLECTED IMAGES

TECHNICAL FIELD

The present invention relates to apparatus and methods for determining the optical quality of optical elements. More particularly, the present invention relates to apparatus and methods for determining the optical quality of optical elements by reflected images.

BACKGROUND ART

Conventional methods of evaluating optical elements utilize the standard Modulation Transform Function (MTF) evaluation and images which are transmitted by refracting optical elements. Such methods which base evaluation on images which are transmitted by refracting optical elements cannot elicit optical quality information about individual surfaces of the optical elements.

The present invention is a novel improvement over previous methods and apparatus for evaluating optical elements which allows for evaluating the contribution of individual optical element surfaces to the overall optical quality of such elements and systems containing such elements.

DISCLOSURE OF THE INVENTION

It is accordingly one object of the present invention to provide a method of evaluating the optical quality of optical elements and optical systems.

It is another object of the present invention to provide a method of evaluating the optical quality of optical elements and optical systems which evaluates the optical contribution of individual optical element surfaces to the overall optical quality of optical elements and optical systems.

Another object of the present invention is to provide a method of evaluating the optical quality of optical elements and optical systems which evaluates reflected images.

A further object of the present invention is to provide a method of evaluating the optical quality of corneas.

A still further object of the present invention is to provide an apparatus for evaluating the optical quality of optical elements and optical systems.

A still further object of the present invention is to provide for an apparatus for evaluating the optical quality of optical elements and optical systems which evaluates the optical contribution of individual optical element surfaces to the overall optical quality of optical elements and optical systems.

An even further object of the present invention is to provide for an apparatus for evaluating the optical quality of optical elements and optical systems which evaluates reflected images.

According these and further objects of the present invention which will become apparent as the description thereof proceeds, the present invention provides for a method of evaluating optical elements which comprises:

projecting an image onto a optical element to be tested so as to form a corresponding reflected image from a surface of the optical element to be tested;

receiving the corresponding reflected image from the optical element to be tested and directing the corresponding reflected image to a video analyzer; and determining the optical quality of the optical element to be tested from the reflected image.

The present invention further provides an apparatus for evaluating optical elements which comprises:

means to form and project a test pattern image onto an optical element to be tested;

means to receive a reflected image from the optical element which corresponds to the collimated step function image;

means to direct the reflected image to a microscope for viewing the reflected image;

a video array connected to the microscope for recording the reflected image; and computer means for determining the optical quality of the optical element from the reflected image.

In a further embodiment, the present invention also provides for a method of evaluating corneas which comprises:

projecting an image onto a cornea so as to form a corresponding reflected image from a surface of the cornea;

receiving the corresponding reflected image from the cornea and directing the corresponding reflected image to a video analyzer; and determining the optical quality of the cornea from the reflected image.

BRIEF DESCRIPTION OF DRAWINGS

Features and characteristics of the present invention will be described hereafter with reference to the attached drawings which are given by way of non-limiting examples in which.

BEST MODE FOR CARRYING OUT THE INVENTION

The present invention is directed to a method of and apparatus for providing information regarding the resolving power and contrast response, and overall optical quality of an optical element and/or optical system. According to the present invention, reflected images are utilized to provide information which is used for evaluating optical elements and/or optical systems.

The method and apparatus of present invention is designed and applicable for evaluating a variety of optical elements and optical systems. Accordingly, the article under test could consist of a simple lens or a multiple element optical system such as an eye. According to one embodiment, it has been discovered that the present invention is particularly useful for evaluating corneal transplants and grafts, and for qualifying the optical quality of a cornea after reshaping procedures.

The present invention utilizes the Modulation Transfer Function (MTF) of a reflected image to evaluate the optical quality of an optical element or optical system under test.

The MTF of a reflected image from either the front or back surface of a single optical element alone or an optical element in an system under test has been found to be useful to describe the contribution of the element or system to the departure from diffraction limited performance. Accordingly, judicious choice of the image under analysis will allow direct evaluation of the reflected image of a front surface, or, by viewing images reflected by interior surfaces, the refractive performance of preceding elements can be determined.

Figure 1:
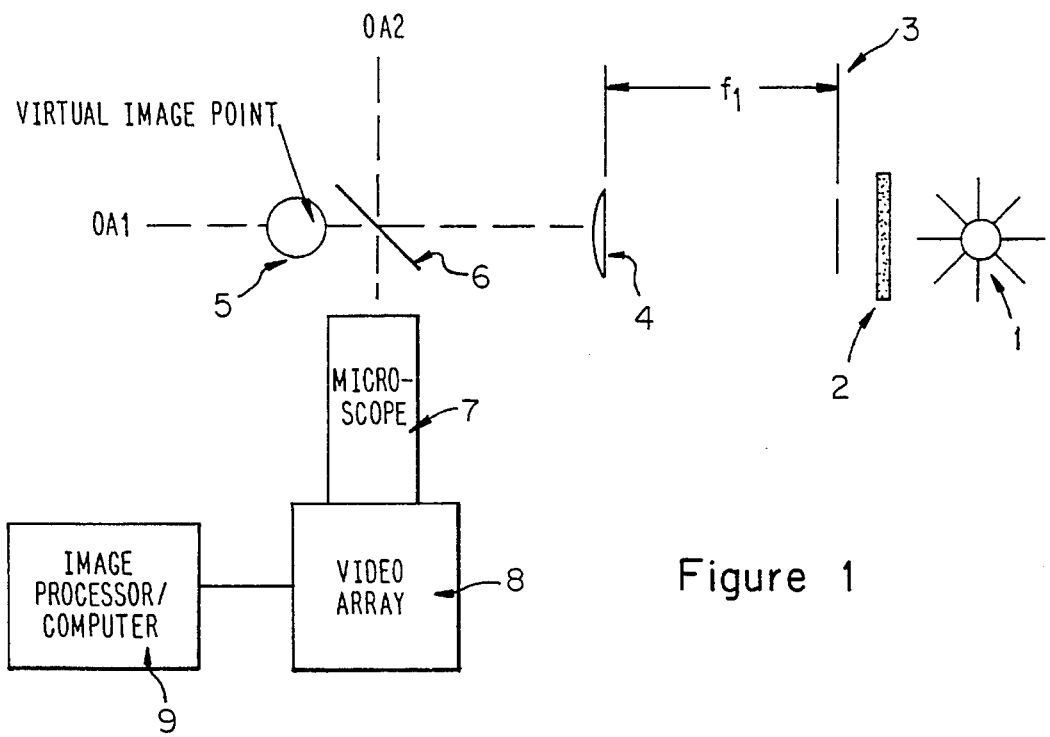
FIG. 1 is a schematic diagram of an apparatus for evaluating a virtual image according to one embodiment of the present invention.

FIG. 1 is a schematic diagram depicting an apparatus for evaluating a virtual image according to one embodiment of the present invention. In FIG. 1 a configuration of the apparatus is depicted in which the virtual reflected image from a positive lens element under test is viewed by a long working distance microscope 7. As depicted, an incoherent, multi-angle illumination source 1 and diffuser 2 are provided to uniformly illuminate a suitable test pattern, e.g. knife-edge mask 3. The incoherent, multi-angle illumination source 1 may comprise any conventional light source, such as an incandescent filament bulb, light emitting diode (LED), or the like, the same not being limiting of the present invention. The diffuser likewise may comprise any type of standard glass or plastic diffuser and may include appropriate condensor optics. However, in a preferred embodiment according to the present invention a ground glass diffuser was found to be particularly suitable.

A collimating lens 4 is positioned at a suitable distance, i.e., the focal length ($f_L$) thereof, from the knife-edge mask 3 so as to project the image of the knife-edge mask 3 to infinity along optical axis OA1. In order to properly position collimating lens 4 with respect to the knife-edge mask 3, it is preferred to use a standard autocollimating mirror (not illustrated), in a known manner.

The collimated, uncorrelated image information from collimating lens 4 is reflected by the optical system under examination 5. Inasmuch as typical elements of interest have a positive focal length, the reflected image diverges from a virtual object point behind the surface of the optical system 5.

A pellicle 6 diverts the image reflected from the optical system 5 along a second optical axis OA2 as illustrated. The intensity of the diverted image should typically be less than about 20% and preferably less than about 8% of the intensity actually reflected by the optical system 5.

A long working distance microscope 7 is positioned along optical axis OA2 so as to view the virtual object image produced by optical system 5. The microscope image is monitored with a high resolution video array 8. The resulting video output from video array 8 is stored in an image processor/computer 9.

After the video image of the virtual object is obtained and stored, the MTF is thereafter performed on a digitized line of the video image to yield a quantitative measure of the resolving power and contrast sensitivity inherent in the reflected image from the optical element of system under test as discussed below.

Figure 2:
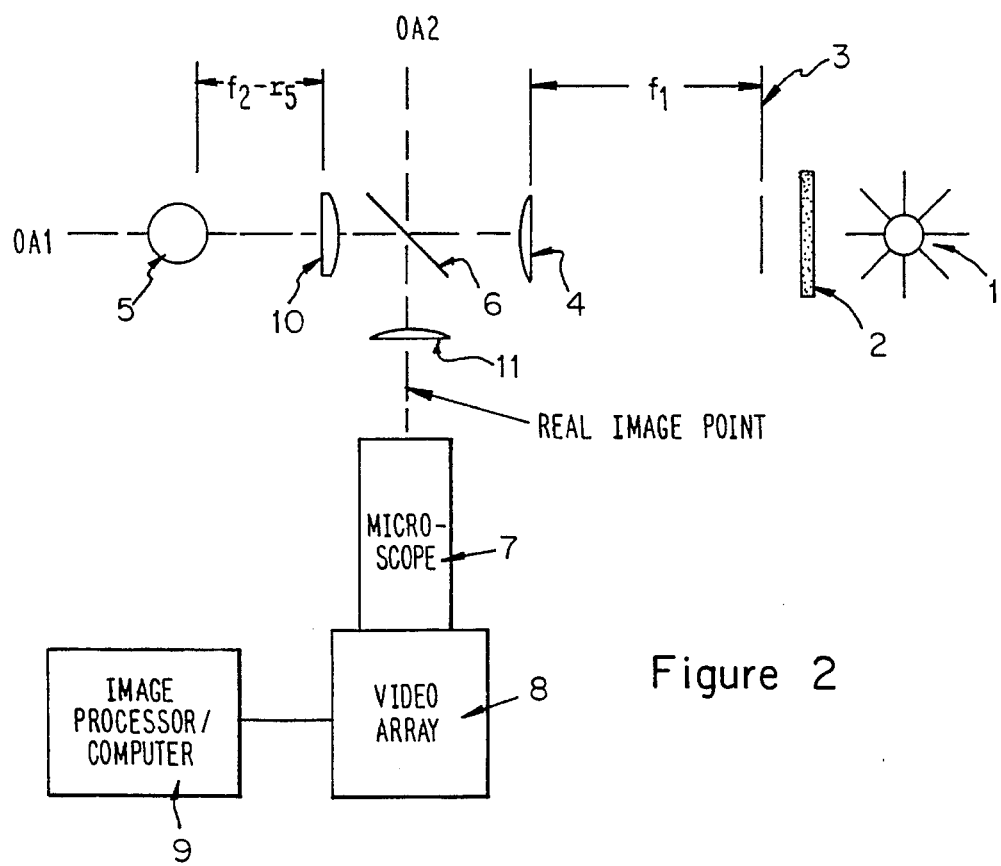
FIG. 2 is a schematic diagram of an apparatus for evaluating a real image according to one embodiment of the present invention.

FIG. 2 is a schematic diagram depicting an apparatus for evaluating a real image according to one embodiment of the present invention. For convenience, like elements are labeled with similar reference numerals in FIGS. 1 and 2. As depicted in FIG. 2 an incoherent, multi-angle illumination source 1 and diffuser 2 are provided to uniformly illuminate a suitable test pattern, e.g. knife-edge mask 3.

A collimating lens 4 is positioned at a suitable distance, i.e., the focal length ($f_1$) thereof, from the knife-edge mask 3 so as to project the image of the knife-edge mask 3 to infinity along optical axis OA1.

The collimated, uncorrelated image information from collimating lens 4 is set to convert by lens 10 to the optical system under examination 5.

According to the embodiment of the present invention depicted in FIG. 2 the reflected real image from the optical system 5 to cause the rays to be reflected back along their original path, i.e., in the example of optical system 5 this distance is the difference between the focal length $f_2$ and the radius of curvature of the positive optical element $r_5$ under test. The resulting collimated image is relayed by pellicle 6 to an imaging lens 11, which forms a real image that is viewed by microscope 7. As in the other embodiments of the present invention, the positions of the collimating lens and imaging lens are preferably set utilizing known autocollimation techniques.

A microscope 7 is positioned along optical axis OA2 to view the real object image produced by optical system 5. The microscope image is monitored with a high resolution video array 8. The resulting video output from video array 8 is stored in an image processor/computer 9 and processed in a similar manner as described below.

Figure 3:
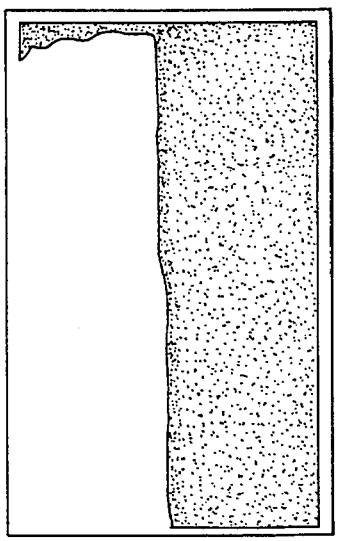
FIG. 3 is a video image of a knife-edge mask as viewed by the video array of FIG. 1.

The image of the knife-edge mask 3 as viewed by the video array 8 is shown in FIG. 3. Once the video image of the knife-edge mask 3, or any suitable step function is obtained, the necessary processing according to the present invention involves first plotting or mathematically determining the intensity of the video image versus the array column for that image, averaged over a suitable number of the lines of the acquired image as necessary to obtain test information.

Figure 4:
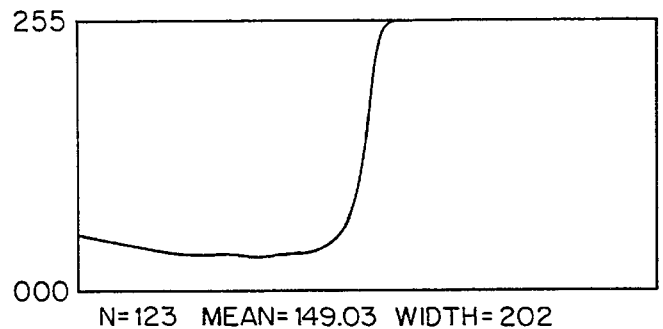
FIG. 4 is a plot the intensity of the image of FIG. 3 versus the array column of the image.

FIG. 4 is an example of such a plot of video image of FIG. 3. The plot in FIG. 4 is a representation of the step function response of the optical system under examination and the imaging instrumentation of the apparatus.

Once the step function response of the optical system under examination is obtained by either plotting the intensity of the video image versus the lines of the acquired image or by performing a similar calculation utilizing the computer, the derivative of the step function response is thereafter calculated. This derivative of the step function response is an estimate of the impulse response of the optical system under examination.

The Fourier transform of the derivative of the step function response is thereafter taken to yield the Modulation Transfer Function (MTF). The MTF for the optical system under examination characterizes the optical system's resolving power and contrast response.

The following example is presented to illustrate features and characteristics of the present invention, which is not to be interpreted as being limited thereto.

EXAMPLE

This example was made to demonstrate the utility of the method of the present invention by comparing two MTFs. In this example a convex surface of a short focal length (35 mm) plano-convex lens was tested according to the method of the present invention with and without a small portion of transparent shrink-wrap plastic covering a portion of the lens.

Figure 5:
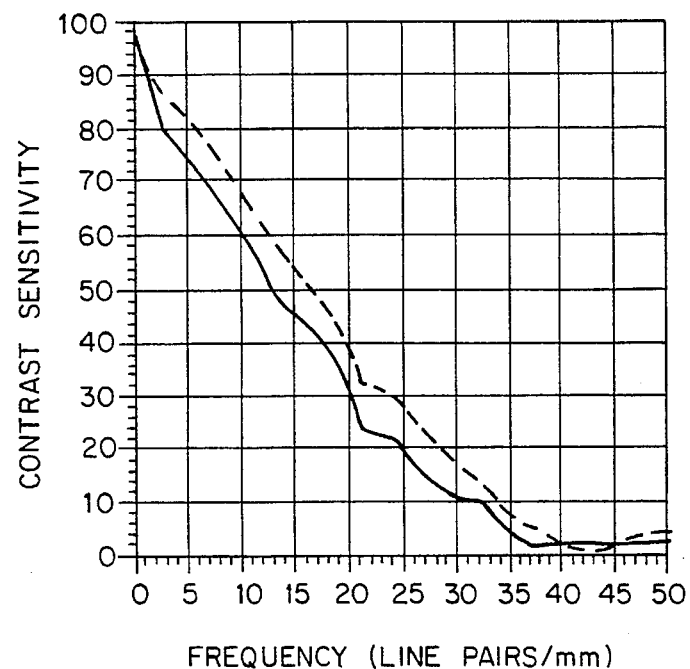
FIG. 5 is a graph which compares MTF results of a lens front surface with and without distortion.

FIG. 5 is a graph comparing MTF results of a lens front surface with and without distortion. In FIG. 5, the dashed line indicates the MTF for the convex surface of a short focal length (35 mm) plano-convex lens. The solid line in FIG. 5 indicates the MTF of the same lens after a small portion of the lens was covered by transparent shrink-wrap plastic.

The distortion introduced by the shrink-wrap is seen in the resulting degradation of contrast sensitivity at lower spacial frequencies. Consequently, these results illustrated in FIG. 5 demonstrate the ability of the method and apparatus of the present invention to detect small nonuniformities and distortions on or in the surfaces of optical elements.

Although the invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims which follow.

What is claimed is:

1. An apparatus for evaluating optical elements which comprises:

means to form and project a collimated test image onto an optical element to be tested;

means to receive a reflected image having an intensity from said optical element which corresponds to said collimated test image;

a microscope for viewing said reflected image;

means to direct said reflected image to a microscope for viewing said reflected image;

a video array connected to said microscope for recording said reflected image; and computer means for determining the optical quality of said optical element from said reflected image.

2. An apparatus for evaluating optical elements according to claim 1, wherein said computer means comprises means to determine resolving power and contrast sensitivity of said optical element.

3. An apparatus for evaluating optical elements according to claim 1, wherein said computer means comprises means to determine Modulation Transfer Function of said reflected image.

4. An apparatus for evaluating optical elements according to claim 1, wherein said reflected image comprises a virtual image.

5. An apparatus for evaluating optical elements according to claim 1, wherein said image comprises a real image and said means to receive and direct said reflected image further includes a collimating lens which directs a collimated, reflected image to a pellicle which diverts said collimated, reflected image to an imaging lens positioned in the optical field of said microscope.

6. An apparatus for evaluating optical elements according to claim 1, wherein said means to receive and direct said reflected image comprises a pellicle which is positioned between said means to form and project said collimated test image and said optical element to be tested.

7. An apparatus for evaluating optical elements according to claim 6, wherein said pellicle diverts less than about 20% of the intensity of said reflected image to said microscope.

* * * * *